United States Patent
Lambert

(10) Patent No.: US 7,841,339 B2
(45) Date of Patent: Nov. 30, 2010

(54) DEVICE AND METHOD FOR RECOVERING ANAESTHETICS

(75) Inventor: Hans Lambert, Stockholm (SE)

(73) Assignee: Sedana Medical AB (SE)

( * ) Notice: Subject to any disclaimer, the term of this patent is extended or adjusted under 35 U.S.C. 154(b) by 1153 days.

(21) Appl. No.: 10/576,521

(22) PCT Filed: Oct. 18, 2004

(86) PCT No.: PCT/SE2004/001500

§ 371 (c)(1),
(2), (4) Date: Apr. 19, 2006

(87) PCT Pub. No.: WO2005/037357

PCT Pub. Date: Apr. 28, 2005

(65) Prior Publication Data

US 2007/0079827 A1 Apr. 12, 2007

(30) Foreign Application Priority Data

Oct. 20, 2003 (SE) .................................. 0302764

(51) Int. Cl.
 *A61M 16/00* (2006.01)
 *A61M 15/00* (2006.01)
 *B05D 7/14* (2006.01)
 *B65D 83/06* (2006.01)
(52) U.S. Cl. .............................. 128/203.15; 128/203.12
(58) Field of Classification Search ............ 128/203.15; 251/283
See application file for complete search history.

(56) References Cited

U.S. PATENT DOCUMENTS

| 4,532,961 | A | * | 8/1985 | Walton et al. ........... 137/625.31 |
| 4,930,498 | A | * | 6/1990 | Hayek ........................... 601/44 |
| 5,044,361 | A | * | 9/1991 | Werner et al. ........... 128/204.16 |
| 5,044,362 | A | | 9/1991 | Younes |
| 5,471,979 | A | | 12/1995 | Psaros et al. |
| 5,950,518 | A | * | 9/1999 | Pfeifer ....................... 91/375 A |
| 5,979,504 | A | * | 11/1999 | Spivey et al. ............. 137/636.1 |
| 6,145,540 | A | * | 11/2000 | Linkner, Jr. ............. 137/625.65 |
| 7,077,136 | B2 | * | 7/2006 | Ahlmén et al. .......... 128/205.27 |
| 7,347,203 | B2 | * | 3/2008 | Marler et al. ........... 128/201.13 |
| 2003/0089116 | A1 | * | 5/2003 | Heron ............................... 62/6 |

FOREIGN PATENT DOCUMENTS

| EP | 0972534 | 1/2000 |
| WO | WO 9714465 | 4/1997 |

* cited by examiner

*Primary Examiner*—Justine R Yu
*Assistant Examiner*—Colin Stuart
(74) *Attorney, Agent, or Firm*—Cantor Colburn LLP

(57) ABSTRACT

The invention relates to a device for recovering anaesthetics in anaesthetic treatment of a patient. The device comprises a housing having a first opening and a second opening for the formation of a flow path in the housing for a breathing medium. In the housing, an absorption body having the capacity of absorbing and desorbing anaesthetics is arranged. According to the invention, there is valve means for the switch-over between an active position, in which the flow path passes through the absorption body, and a passive position, in which the flow path does not pass through the absorption body. The absorption body retains unchanged location in the housing in both valve positions. The invention also relates to a method for, in a corresponding way, controlling a device for recovering anaesthetics.

1 Claim, 4 Drawing Sheets

DEVICE AND METHOD FOR RECOVERING ANAESTHETICS

FIELD OF THE INVENTION

From a first aspect, the present invention relates to a device for recovering anaesthetics in anaesthetic treatment of a patient, which device comprises a housing having a first opening and a second opening for the formation of a flow path in the housing for a breathing medium, and further comprises an absorption body arranged in the housing and having the capacity of absorbing and desorbing anaesthetics.

From a second aspect, the invention relates to a method for controlling a device for recovering anaesthetics, which device comprises a housing having a first and a second opening for the formation of a flow path in the housing for a breathing medium, and further comprises an absorption body arranged in the housing and having the capacity of absorbing and desorbing anaesthetics.

BACKGROUND OF THE INVENTION

In anaesthetic treatment of patients that are connected to a respirator, anaesthetic is added to the inhalation medium that may be air or oxygen. In the following, for the sake of simplicity the term air is used, but applies also with regard to oxygen. Upon exhalation, a part of the anaesthetic trails the exhalation air. Traditionally, this exhaled anaesthetic was lost.

In order to improve the economy in anaesthetic treatment, it has been known for a long time to take actions for recovering exhaled anaesthetic. This is based on the provision of an anaesthetic absorber in the breathing pipe having the function of being able to absorb anaesthetic upon exhalation and to desorb the absorbed anaesthetic upon inhalation. Accordingly, the anaesthetic that is supplied to the patient upon inhalation is composed of continuously supplied new anaesthetic as well as of anaesthetic recovered by the device. Such a device is disclosed in, among others, U.S. Pat. No. 5,044,362.

A disadvantage of such a device is that when the anaesthetic treatment is to be terminated and consequently supply of new anaesthetic to the breathing pipe is turned off, still a certain supply of anaesthetic will proceed. This is because, upon each inhalation, the absorbed anaesthetic is released and supplied to the patient. However, the amount of anaesthetic that subsequently being exhaled and absorbed again decreases for each breath, since a part is absorbed by the patient. Therefore, the supply of anaesthetic will decay gradually. This takes place during a space of time of some minutes.

The consequence becomes that the point of time for awakening after the anaesthetic treatment becomes diffuse, and the patient will be anaesthetized a couple of minutes in excess of what is required. As an alternative, the (nurse) anaesthetist may turn off the supply of anaesthetic a couple of minutes in advance. However, this implies increased demands on the (nurse) anaesthetist and creates the risk of faulty manipulation and faulty timing as regards the turn off.

By EP 855924, a device is previously known that partly takes this problem into account. Hence, in the device disclosed therein, the absorption body is rotatable in the housing so that it either is turned in a way so that the absorption body is active or in a way so that the breathing gas passes around the absorption body. In the latter position, the absorption body is mainly passive and absorbs only very little anaesthetic. However, the known device has certain disadvantages such as that the absorption body may run the risk of ending up in intermediate positions, that it may become damaged while turning. Moreover, the flow duct becomes narrow in the passive position. Finally, the construction presumes a relatively extended absorption body, which causes high flow resistance in the active position.

Therefore, the object of the present invention is to provide a device for the supply of anaesthetic to a patient enabling a complete cut off of the supply of anaesthetic to the patient when the supply of new anaesthetic is cut off, without being impaired by the disadvantages that are inherent in previously known devices of similar type.

SUMMARY OF THE INVENTION

In a first aspect of the invention, the object set up has been attained by the fact that a device of the kind defined in the preamble of claim 1 comprises the special features that the device comprises valve means that is adjustable between an active position, in which the flow path passes through the absorption body, and a passive position, in which the flow path does not pass through the absorption body, and wherein the absorption body retains unchanged location in the housing in both valve positions.

Thanks to such an arrangement, it is possible to cut off the supply of anaesthetic to the patient entirely without time delay. During the treatment, the device is in the active position thereof, recovering of anaesthetic taking place according to the principle described above. The moment that the device is switched over to the passive position thereof, this resupply of anaesthetic ceases. By switching over the device at the same time as the supply of new anaesthetic is cut off, an immediate total cut off of supply of anaesthetic to the patient is effected. Accordingly, any time delay that has been described above does not occur. Furthermore, the arrangement involves that two clearly distinct positions are provided, so that the risk of faulty adjustment is eliminated. Since the absorption body is not displaced from the position thereof, moreover the risk of damaging the same is avoided. Further, it is made possible to form the flow paths optimally in the active as well as in the passive position.

According to a preferred embodiment, the valve means comprises a rotatable unit. Thereby, switch-over can be achieved by a simple rotary motion of the rotatable unit, with the risk of faulty operation being very small.

According to an additional preferred embodiment, one of the openings is arranged at the rotatable unit, said opening in a first rotational position of the unit mouthing in the housing on schematic of the absorption body and in a second rotational position mouthing on the other side of the absorption body.

This presents a structurally simple solution with favourable flow conditions.

According to an additional preferred embodiment, the housing has the form of a box having a height that is smaller than the smallest extension thereof transverse to the height, and the absorption body is plate-shaped and is in the active position thereof substantially perpendicular to the height, and wherein each opening has a flow direction that is substantially parallel to the absorption body. By virtue of such a construction, it is attained that the housing gets relatively small dimensions in relation to the extension of the absorption body, that a relatively large flow area of the absorption body is obtained, and that the flow conditions become favourable in order to readily be able to achieve switch-over of the flow path.

According to an additional preferred embodiment, the two flow paths are concentrically arranged in relation to each other.

This entails that the unit can be made compact and that the flow paths can be established with very small changes of direction.

According to an additional preferred embodiment, the absorption body is arranged in the radially outer flow path.

Normally, the flow path through the absorption body requires a larger flow area than the free flow area. By locating the absorption body farthest out, the unit can be made with a smaller diameter than in the opposite arrangement. This is, because of reasons of flow mechanics it is not possible to have too a small spacing between the walls of the flow path.

According to an additional preferred embodiment, the valve means comprises a first and a second unit rotatable in relation to each other and adjacent to each other, which first unit comprises an even number of sections distributed in the circumferential direction, each section comprising a wall member and an opening, where in every second section the opening is situated radially outside the wall member and in every second section the opening is situated radially inside the wall member, and which second unit comprises an even number of portions distributed in the circumferential direction, where every second portion consists of a fully covering wall and every second consists of an opening.

Such a construction of the valve is a simple and handy solution for distributing the flow to either of two concentric flow paths.

According to an additional preferred embodiment, the number of sections is eight or greater and the number of portions equal to the number of sections, and each section and each portion being of substantially triangular shape and each opening and each wall member being of substantially triangular or trapezoidal shape.

By having a relatively great number of sections and portions, an efficient and evenly distributed distribution is attained in the circumferential direction.

According to an additional preferred embodiment, each of said units is of conical shape.

Thereby, walls are obtained that are obliquely directed in the direction of flow, which decreases the flow resistance of the valve.

According to the second aspect of the invention, the object set up has been attained by the fact that a method of the kind defined in the preamble of claim 9 comprises the particular measures of directing the flow in the flow path by virtue of a valve means in order to either pass through the absorption body or beside the same and that the location of the absorption body thereby is retained unchanged.

According to preferred embodiments of the invented method, the same is exercised while using the invented device:

By virtue of the invented method, advantages of the type corresponding to what has been stated above for the invented device and preferred embodiments of the same are gained.

The invention is explained closer by the appended detailed description of advantageous embodiments of the same, reference being made to the appended drawing figures.

DESCRIPTION OF ADVANTAGEOUS EMBODIMENT EXAMPLES

Figure 1:
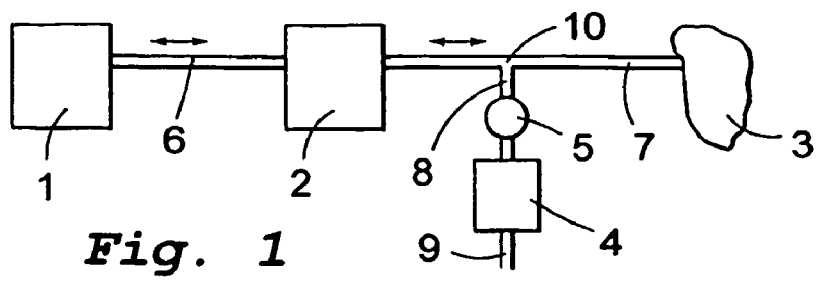
FIG. 1 is a schematic view of a device according to prior art.

In FIG. 1, 1 symbolizes a respirator, 2 a device for recovering anaesthetics, 3 a patients lungs, 4 an anaesthetic vaporizer, and 5 a valve.

Upon inhalation, breathing medium, e.g., air from the respirator 1, is brought through the pipe 6 to the recovering device 2 and further through the patient pipe 7 to the lungs 3 of the patient. Through a pipe 9, liquid anaesthetic is supplied to the anaesthetic vaporizer 4 and, via the valve 5 and the pipe 8, the vaporized anaesthetic is brought to the patient pipe 7 for being mixed with the inhalation air at the connection 10.

Upon exhalation, the air flows from the lungs 3 via the recovering device 2 to the respirator 1. Anaesthetic not having been assimilated by the patient trails the exhalation air and a part of this is absorbed in the recovering device 2.

Upon next inhalation, when the air flows from the respirator 1 to the lungs 3 of the patient, a part of the absorbed anaesthetic is given off from the recovering device 2 to the inhalation air passing by and is brought, together with newly supplied anaesthetic from the vaporizer 4, to the patient with the inhalation air.

When the anaesthetic treatment is to be terminated, the valve 5 is closed, supply of new anaesthetic ceasing. However, supply of anaesthetic from the recovering device 2 continues in decreasing degree.

In FIGS. 2-15, there is shown some advantageous embodiment examples of a recovering device intended to replace the recovering device 2 in FIG. 1.

Figure 2:
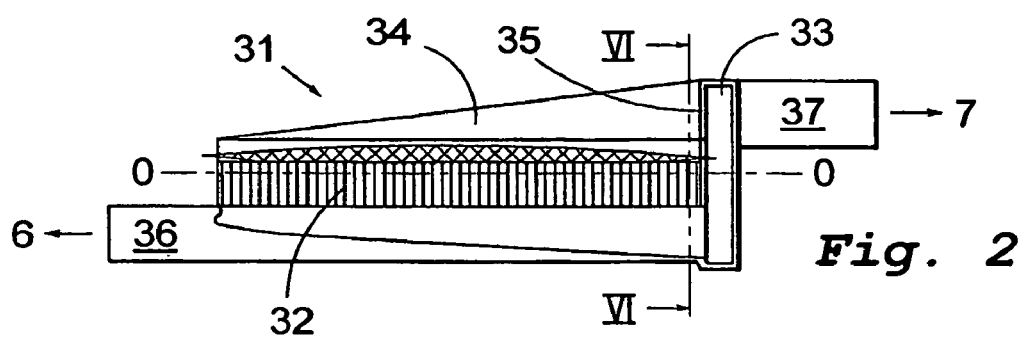
FIG. 2 is a schematic section through a first embodiment example of a device according to the invention in a first position.

In FIG. 2, a first embodiment example of a device according to the invention is illustrated. Here, the housing 31 is composed of a main member 34 and a valve member 33, which valve member constitutes a valve means of the device. In the main member 34, there is an opening 36 for the connection with a pipe 6 to the respirator, and in the valve member 33 there is an opening 37 for the connection with a patient pipe 7. In the main member 34, an absorption body 32 is arranged and divides the main member 34 in an upper and a lower chamber.

Figure 4:
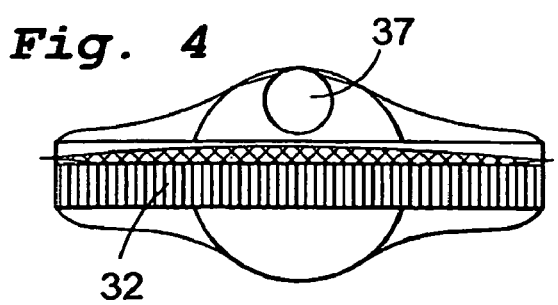
FIG. 4 is a section along the line VI-VI in FIG. 2.

The main member 34 and the valve member 33 can be turned in relation to each other around an axis of rotation 0-0. The main member 34 and the valve member communicate with each other through an opening 35 located right opposite the opening 37. In FIG. 4, hence the patient pipe 7 communicates with the upper chamber of the main member 34, and pipe 6 to the respirator with the lower chamber thereof. This represents the active position of the device where the flow is forced through the absorption body 32 for the absorption and desorption of anaesthetic, such as has been described above.

Figure 3:
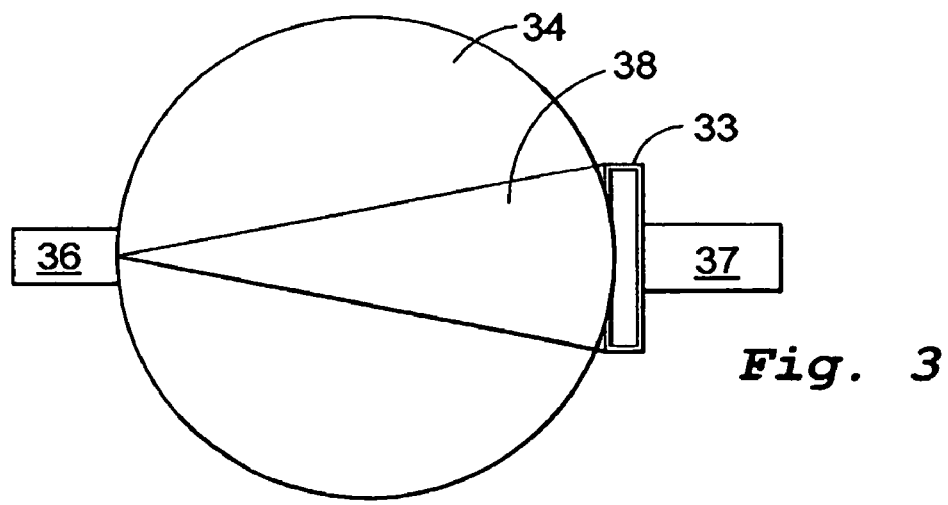
FIG. 3 is a schematic view from above of the device according to FIG. 2.

As is seen in FIG. 3, the housing has a substantially circular shape having a back 38 of triangular shape arranged on the top side.

The position shown in FIG. 2 is illustrated in an end view in FIG. 4.

Figure 5:
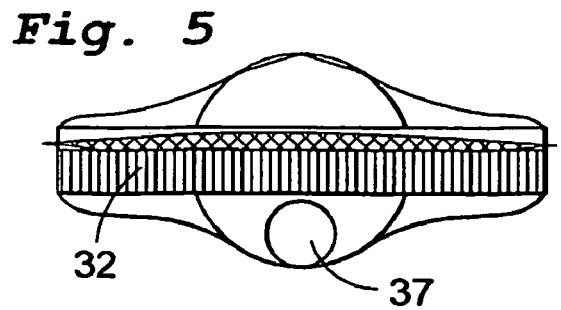
FIG. 5 is a section corresponding to that in FIG. 4 with the device being in a second position.

In FIG. 5, a position with the valve member 33 having been turned a half revolution in relation to the main member 34 is shown in a corresponding end view. Now, the opening 37 connected with the patient pipe communicates with the main member 34 of the housing. Thereby a direct flow path between the openings 36 and 37 is established, without passage through the absorption body 32. Hence, the device is in the passive position thereof.

Figure 6:
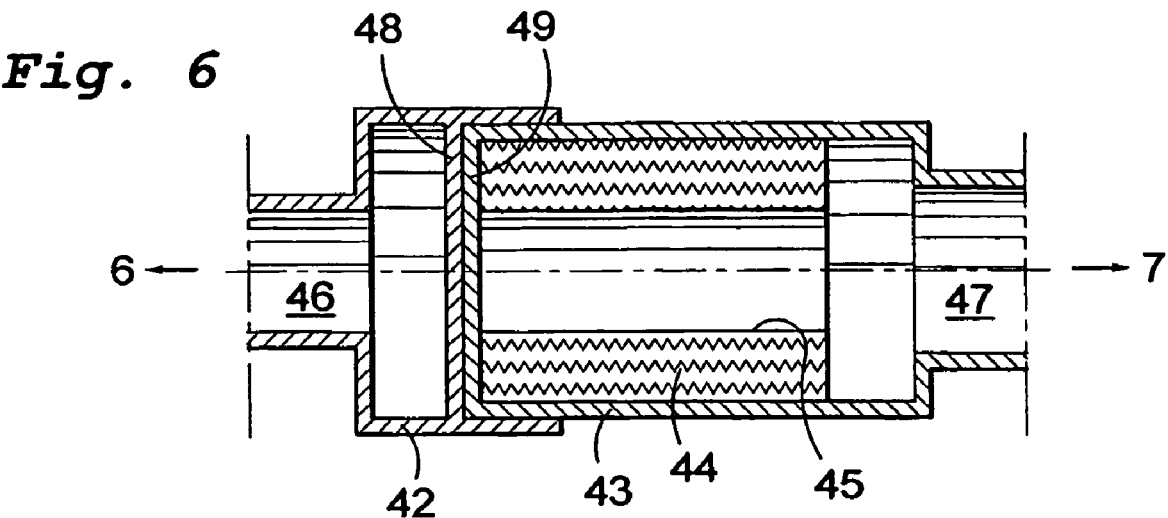
FIG. 6 is a longitudinal section through a second embodiment example of the invention.

FIG. 6 is a longitudinal section through a schematic illustration of a second embodiment example of the invention. The housing is composed of a first member 42 and a second member 43, each of which is connected to a respirator 6 and a patient pipe 7, respectively, via an opening 46 and 47, respectively. The housing members 42 and 43 are rotatable in relation to each other, and in the right housing member 43, the absorption body is 44 arranged. The same is formed as a hollow cylinder having a through hole 45.

A first plate 48 is fixedly connected to the housing member 42, and a second plate 49 is fixedly connected to the housing member 43. Each plate is provided with openings arranged so that when the plates are in a first rotational position in relation to each other, a flow path through the absorption body 44 is formed while flow through the central hole 45 is blocked. In a second rotational position, the openings end up in such a position that a flow path through the central hole 45 is formed while the flow through the absorption body 44 is blocked. How the openings in the plates 48, 49 are arranged for the achievement of the same alternative flow paths is seen in FIG. 7 and 8.

Figure 7:
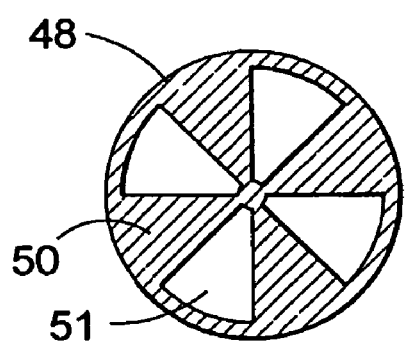
FIG. 7 is a section through a first detail in the device in FIG. 6.

FIG. 7 is a section through the plate 48 in the left housing member 42.

The plate 48 is composed of eight portions, each of which constituting a segment of 45°. Every second portion 50 entirely consists of a wall constituting a part of the plate. Every second portion 51 substantially consists of an opening.

Figure 8:
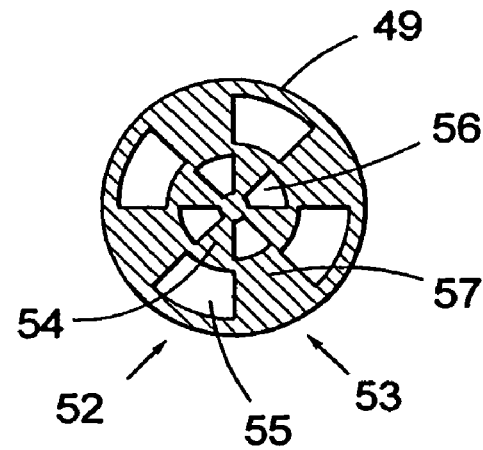
FIG. 8 is a section through a first detail in the device in FIG. 6.

FIG. 8 is a corresponding section through the plate 49 in the right housing member 43. The plate 49 is composed of eight sections, each of which constituting a segment of 45°. Every second section 52 is composed of a radially inner part that consists of a wall 54 and a radially outer part that consists of an opening 55. Every second section 53 is composed of a radially inner part that consists of an opening 56 and a radially outer part that consists of a wall 57.

Figure 9:
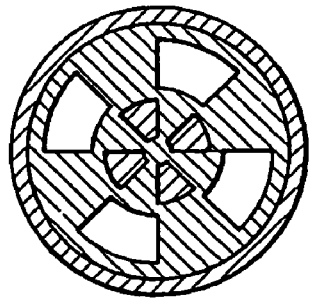
FIG. 9 and 10 illustrates co-operation between the details in FIG. 7 and 8 in two different positions.

In a first rotational position, the plates 48, 49 are located so that the portions 51 and the sections 52 cover each other and the portions 50 and the sections 53 cover each other. Thereby, a pattern of overlapping openings and walls arises, which is illustrated in FIG. 9, where the shaded parts indicate wall. Hence, flow path is established through the radially outer the part, i.e., through the absorption body 44 (FIG. 6).

Figure 10:
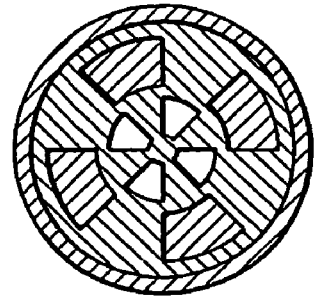
Figure 11:
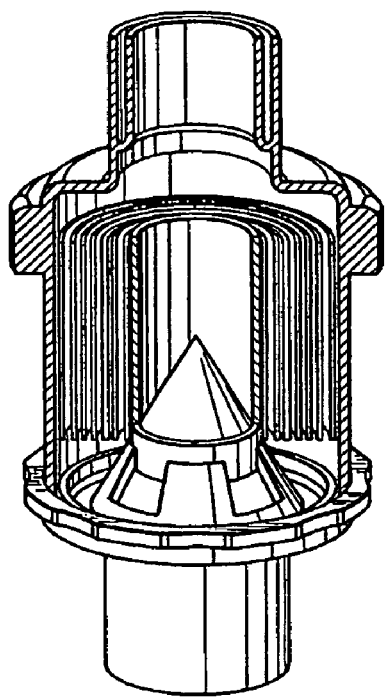
FIG. 11 and 12 are perspective views of additional embodiment examples of the invention.
Figure 12:
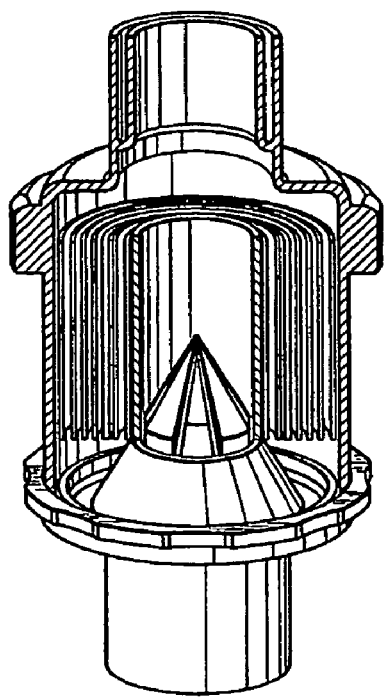
Figure 13:
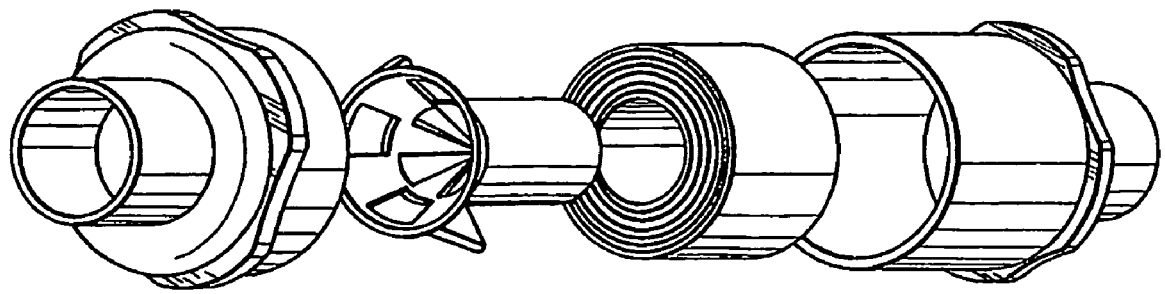
FIG. 13 is an exploded view of the device according to FIG. 11.
Figure 14:
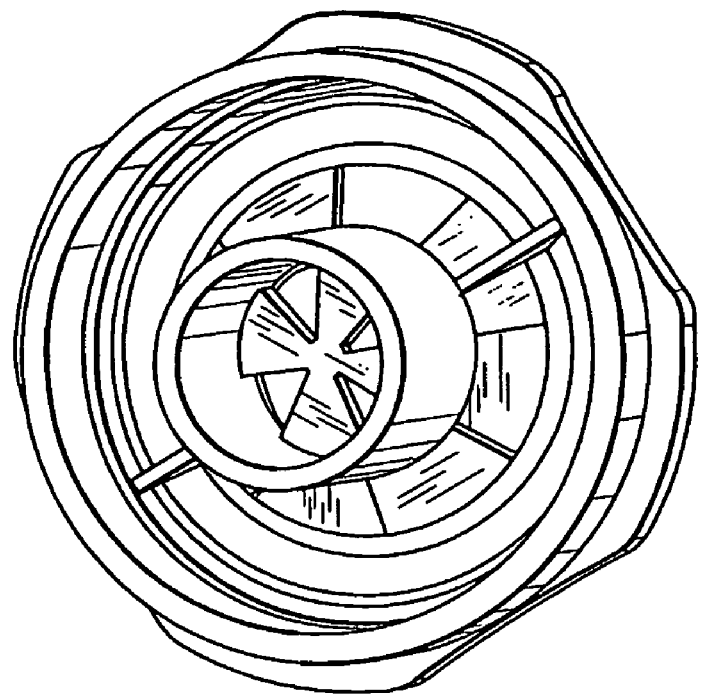
FIG. 14 is a perspective view from the inside of the housing of a detail in FIG. 13 illustrating a first valve position.
Figure 15:
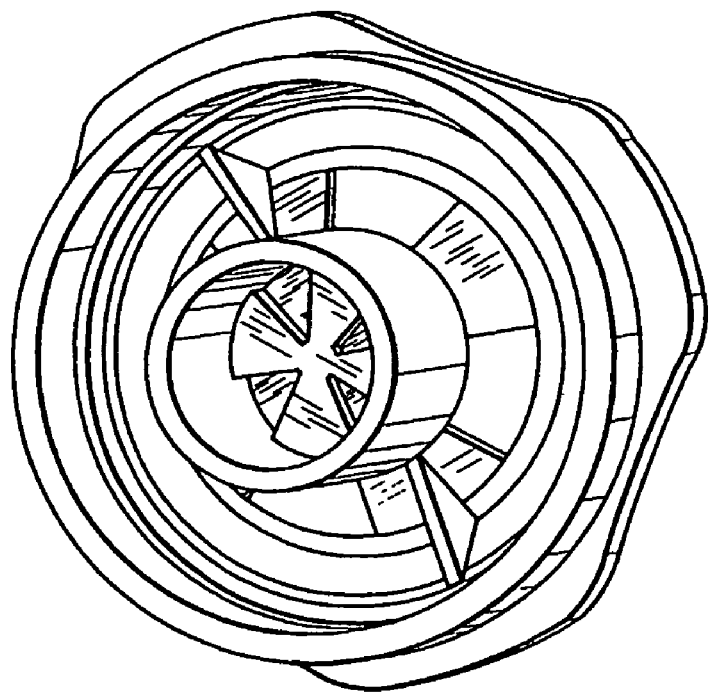
FIG. 15 is a perspective view corresponding to that of FIG. 15 but illustrating a second valve position.

In a second rotational position, 45° from that illustrated in FIG. 9, the plates 48, 49 are located so that the portions 51 and the sections 57 cover each other and the portions 50 and the sections 52 cover each other. Thereby, a pattern of overlapping openings and walls arises, which is illustrated in FIG. 10, where the shaded portions indicate wall. Hence, flow path is established through the radially inner part, i.e., through the hole 45 (FIG. 6).

The plates 48 and 49 may advantageously be replaced by conical elements having the corresponding orientation of openings and wall members. FIGS. 11-15 illustrate different examples of such an embodiment.

The invention claimed is:

1. Device for recovering anaesthetics in anaesthetic treatment of a patient, which device comprises;
   a housing having a first opening and a second opening for formation of a flow path to and from the patient in the housing for a breathing medium,
   an absorption body arranged in the housing and having a capacity of absorbing and desorbing anaesthetics,
   a valve means comprising a rotatable unit that is adjustable between an active position, in which a flow path to and from the patient passes through the absorption body, and a passive position, in which a flow path to and from the patient passes through the housing without passing through the absorption body, wherein the absorption body retains unchanged location in the housing in both valve positions,
   wherein one of said openings is arranged at the rotatable unit, said opening being in a first rotational position on a side of the absorption body and in a second rotational position on an opposite side of the absorption body,
   wherein the housing is in the form of a box having a height that is smaller than a smallest extension thereof transverse to the height,
   wherein the absorption body is plate-shaped and is in the active position thereof substantially perpendicular to the height, and
   wherein the housing is configured such that, in both the active and passive positions, air flows from each opening in a flow direction that is substantially parallel to a plane defined by a plate-shaped surface of the absorption body.

\* \* \* \* \*